(12) United States Patent
Ferdosi et al.

(10) Patent No.: US 10,448,849 B2
(45) Date of Patent: Oct. 22, 2019

(54) CONTEXTUAL HEART RATE MONITORING

(71) Applicant: Vital Connect, Inc., Campbell, CA (US)

(72) Inventors: Nima Ferdosi, San Jose, CA (US); Ravi Narasimhan, Sunnyvale, CA (US); Alexander Chan, Campbell, CA (US)

(73) Assignee: Vital Connect, Inc., San Jose, CA (US)

( * ) Notice: Subject to any disclaimer, the term of this patent is extended or adjusted under 35 U.S.C. 154(b) by 752 days.

(21) Appl. No.: 13/842,842

(22) Filed: Mar. 15, 2013

(65) Prior Publication Data

US 2014/0276127 A1  Sep. 18, 2014

(51) Int. Cl.
*A61B 5/0245* (2006.01)
*A61B 5/11* (2006.01)
*A61B 5/0205* (2006.01)

(52) U.S. Cl.
CPC .......... *A61B 5/0245* (2013.01); *A61B 5/0205* (2013.01); *A61B 5/1118* (2013.01)

(58) Field of Classification Search
None
See application file for complete search history.

(56) References Cited

U.S. PATENT DOCUMENTS

| | | | |
|---|---|---|---|
| 6,487,442 B1 * | 11/2002 | Wood | A61B 5/0468 600/515 |
| 2006/0030892 A1 | 2/2006 | Kadhiresan et al. | |
| 2006/0032315 A1 | 2/2006 | Saalastic | |
| 2007/0142715 A1 * | 6/2007 | Banet | A61B 5/0006 600/301 |
| 2009/0076559 A1 * | 3/2009 | Libbus | A61N 1/046 607/6 |
| 2009/0287103 A1 * | 11/2009 | Pillai | A61B 5/0245 600/509 |

(Continued)

FOREIGN PATENT DOCUMENTS

| | | |
|---|---|---|
| JP | 7327942 A | 12/1995 |
| JP | 11178804 H | 7/1999 |

(Continued)

OTHER PUBLICATIONS

Nishime, Erna Obenza, et al. "Heart rate recovery and treadmill exercise score as predictors of mortality in patients referred for exercise ECG." Jama 284.11 (2000): 1392-1398.*

(Continued)

*Primary Examiner* — Patricia Mallari
*Assistant Examiner* — Jairo H Portillo
(74) *Attorney, Agent, or Firm* — Brundidge & Stanger, P.C.

(57) ABSTRACT

A method and system for contextual heart rate monitoring are disclosed. In a first aspect, the method comprises calculating a heart rate using a detected ECG signal and detecting an activity level. In a second aspect, the system comprises a wireless sensor device coupled to a user via at least one electrode, wherein the wireless sensor device includes a processor and a memory device coupled to the processor, wherein the memory device stores an application which, when executed by the processor, causes the processor to calculate a heart rate using a detected ECG signal and to detect an activity level.

16 Claims, 7 Drawing Sheets

(56) References Cited

U.S. PATENT DOCUMENTS

| | | | |
|---|---|---|---|
| 2009/0325766 A1* | 12/2009 | Kasama | A61B 5/024 |
| | | | 482/8 |
| 2011/0105860 A1* | 5/2011 | Houben | A61B 5/0205 |
| | | | 600/301 |
| 2011/0166463 A1 | 7/2011 | Xi | |
| 2011/0190646 A1 | 8/2011 | Kato et al. | |
| 2012/0157861 A1 | 6/2012 | Jarverud et al. | |
| 2012/0172681 A1 | 7/2012 | Sun et al. | |
| 2013/0041590 A1 | 2/2013 | Burichi | |
| 2015/0265160 A1 | 9/2015 | Kato et al. | |

FOREIGN PATENT DOCUMENTS

| | | |
|---|---|---|
| JP | 2000051157 A | 2/2000 |
| JP | 2001198095 A | 7/2001 |
| JP | 2003220039 A | 8/2003 |
| JP | 2004502478 A | 1/2004 |
| JP | 2009027638 A | 2/2009 |
| JP | 2010057678 A | 3/2010 |
| JP | 2011514831 A | 5/2011 |
| JP | 2011172903 A | 9/2011 |
| WO | 2011161599 A1 | 12/2011 |

OTHER PUBLICATIONS

Scruggs, Philip W., Sandy K. Beveridge, and Brian D. Clocksin. "Tri-axial accelerometry and heart rate telemetry: relation and agreement with behavioral observation in elementary physical education." Measurement in Physical Education and Exercise Science 9.4 (2005): 203-218.*

PCT International Search Report and Written Opinion of the International Searching Authority, dated Sep. 11, 2014, application No. PCT/US2014/029082.

Japanese Office Action (Notice of Reasons for Rejection) dated Sep. 13, 2016.

Notice of Reasons for Rejection from Japanese Appln. No. 2017-211913 dated Oct. 9, 2018.

Extended European Search Report dated Feb. 17, 2017.

Extended European Search Report dated Nov. 23, 2018.

* cited by examiner

Figure 7

CONTEXTUAL HEART RATE MONITORING

FIELD OF THE INVENTION

The present invention relates to sensors, and more particularly, to a sensor device utilized for contextual heart rate monitoring.

BACKGROUND

A sensor device can be placed on the upper-body of a user (e.g. chest area) to sense an electrocardiogram (ECG) signal through electrodes that are attached to the skin of the user. The ECG signal is used to measure a variety of health related features of the users including the user's heart rate. The sensor device can also detect the user's motions through an embedded microelectromechanical systems (MEMS) sensor. The data detected from the MEMS sensor is used to measure the user's activity level.

Conventional devices measure heart rate alone to assess the user's health without the context of the user's activity level. For example, a high heart rate (120+ beats per minute or bpm) could signal a cardiovascular condition during rest but is normal during exercise. A low heart rate (<60 bpm) could signal a cardiovascular condition if detected during strenuous exercise but is normal during rest. However, conventional devices are not aware of the user's activity when making heart rate measurements. Therefore, there is a strong need for a cost-effective solution that overcomes the above issues. The present invention addresses such a need.

SUMMARY OF THE INVENTION

A method and system for contextual heart rate monitoring are disclosed. In a first aspect, the method comprises calculating a heart rate using a detected ECG signal and detecting an activity level.

In a second aspect, the system comprises a wireless sensor device coupled to a user via at least one electrode, wherein the wireless sensor device includes a processor and a memory device coupled to the processor, wherein the memory device stores an application which, when executed by the processor, causes the processor to calculate a heart rate using a detected ECG signal and to detect an activity level.

BRIEF DESCRIPTION OF THE DRAWINGS

The accompanying figures illustrate several embodiments of the invention and, together with the description, serve to explain the principles of the invention. One of ordinary skill in the art will recognize that the embodiments illustrated in the figures are merely exemplary, and are not intended to limit the scope of the present invention.

DETAILED DESCRIPTION

The present invention relates to sensors, and more particularly, to a sensor device utilized for contextual heart rate monitoring. The following description is presented to enable one of ordinary skill in the art to make and use the invention and is provided in the context of a patent application and its requirements. Various modifications to the preferred embodiment and the generic principles and features described herein will be readily apparent to those skilled in the art. Thus, the present invention is not intended to be limited to the embodiments shown but is to be accorded the widest scope consistent with the principles and features described herein.

Accurately detecting a user's heart rate within various contexts is important for diagnosing various cardiovascular diseases. A recovery heart rate is the heart rate measured at a fixed period after the user ceasing activity (e.g. exercise). The recovery heart rate is typically measured over a one minute time reference period. A greater reduction in heart rate after the activity during the time reference period indicates a better-conditioned heart. It is not possible to automatically measure the recovery heart rate without measuring the user's activity levels.

A method and system in accordance with the present invention utilizes a wireless sensor device attached to a user to detect at least an ECG signal and an activity level of the user. The wireless sensor device utilizes fusion of user's past and current heart rate and activity level measurements to generate warnings in a variety of situations including but not limited to if the user's heart rate is higher than a given threshold during rest and if the user's heart rate remains below a given threshold during physical activity. The wireless sensor device also automatically measures and tracks the user's recovery heart rate. In one embodiment, predetermined time values (e.g. T1, T2, T3, T4, T5, etc.) and threshold values (Threshold1, Threshold2, Threshold3, Threshold4, Threshold5, etc.) are set by the user. In another embodiment, the predetermined time values and threshold values are set by the wireless sensor device or another external remote system.

One of ordinary skill in the art readily recognizes that a variety of wireless sensor devices can be utilized to measure ECG signals and activity levels including portable wireless sensor devices with embedded circuitry in a patch form factor and that would be within the spirit and scope of the present invention.

To describe the features of the present invention in more detail, refer now to the following description in conjunction with the accompanying Figures.

Figure 1:
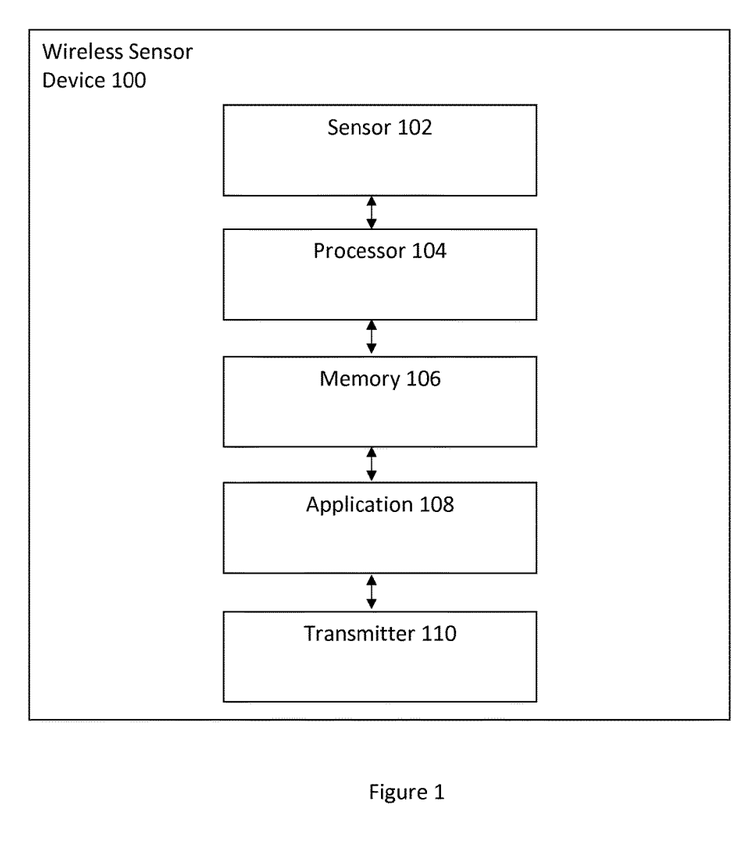
FIG. 1 illustrates a wireless sensor device in accordance with an embodiment.

FIG. 1 illustrates a wireless sensor device 100 in accordance with an embodiment. The wireless sensor device 100 includes a sensor 102, a processor 104 coupled to the sensor 102, a memory 106 coupled to the processor 104, an application 108 coupled to the memory 106, and a transmitter 110 coupled to the application 108. The sensor 102 obtains data (e.g. ECG signal and activity level) from the user and transmits the data to the memory 106 and in turn to the application 108. The processor 104 executes the application 108 to process ECG signal and activity level information of the user. The information is transmitted to the transmitter 110 and in turn relayed to another user or device.

In one embodiment, the sensor 102 comprises two electrodes to measure the ECG signal and a MEMS device (e.g. accelerometer) to record physical activity levels and the processor 104 comprises a microprocessor. One of ordinary skill in the art readily recognizes that a variety of devices can be utilized for the processor 104, the memory 106, the application 108, and the transmitter 110 and that would be within the spirit and scope of the present invention.

In one embodiment, the wireless sensor device 100 measures a heart rate reserve (HRR) and activity level of the user. The HRR is defined by the following equation: HRR= (Heart Rate (HR)−Resting Heart Rate)/(Maximum Heart Rate−Resting Heart Rate). The Maximum Heart Rate is defined by the following equation: Maximum Heart Rate=208−0.7*User's Age.

After measuring the HRR data and the activity level data, the wireless sensor device 100 stores the data over a predetermined window of time (T_WINDOW). For a warning to be generated by the wireless sensor device 100, a combination of the HRR and the activity level data must stay within a region of an Activity/HRR plane for more than a predefined percentage of time (P) over T_WINDOW seconds. In one embodiment, P is 90% and T_WINDOW is 300 seconds.

Figure 2:
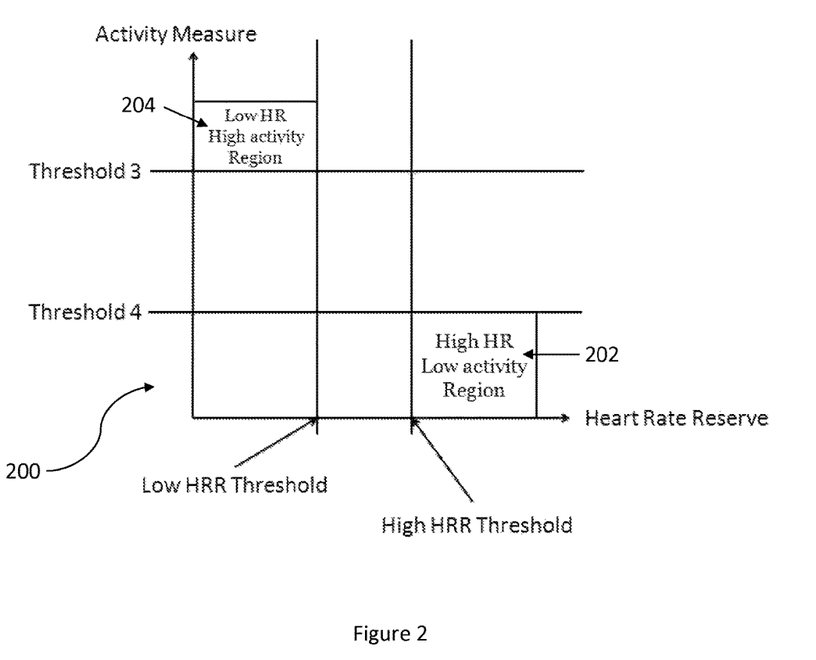
FIG. 2 illustrates a graph plotting HRR and activity level in an Activity/HRR plane in accordance with an embodiment.

FIG. 2 illustrates a graph 200 plotting HRR and activity level in an Activity/HRR plane in accordance with an embodiment. In FIG. 2, a high heart rate and low activity level region that generates a warning is denoted by 202 and a low heart rate and high activity level region that generates a warning is denoted by 204. The high and low thresholds of HRR are determined based on a user's age and the high and low thresholds of heart rate set by the user. Threshold 3 denotes a high activity level threshold and Threshold 4 denotes a low activity level threshold.

Figure 3:
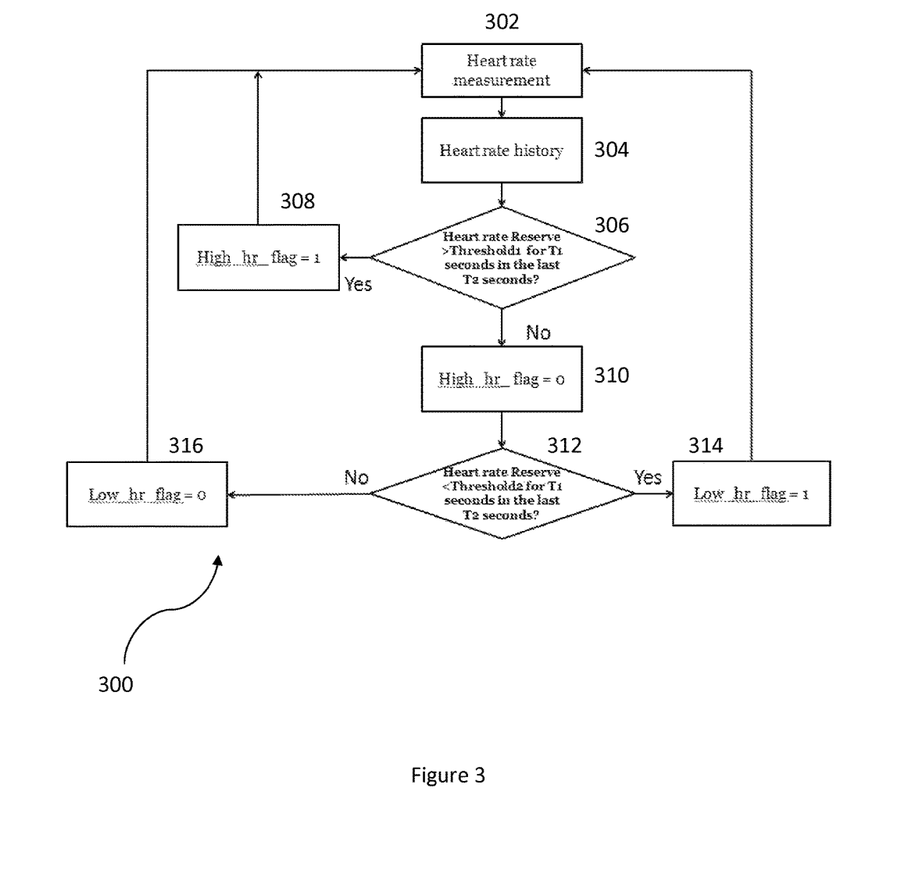
FIG. 3 illustrates a flowchart for measuring heart rates by a wireless sensor device in accordance with an embodiment.

In one embodiment, the wireless sensor device 100 calculates low and high heart rates based upon the detected ECG signal. FIG. 3 illustrates a flowchart 300 for measuring heart rates by a wireless sensor device in accordance with an embodiment. In FIG. 3, the heart rate of a user attached to the wireless sensor device is measured, via step 302, and the user's heart rate history is analyzed to compute the Heart Rate Reserve (HRR) and stored, via step 304. Heart rate values over a predetermined time period (T2 seconds) are stored and used to determine low and high heart rates.

In FIG. 3, it is determined whether the HRR is greater than a threshold (Threshold1) for more than a predefined percentage (P) of time (T1 seconds of the predetermined time period T2), via step 306. If yes (HRR>Threshold1 over P), then High_hr_flag is set to 1 denoting that a high heart rate has been detected, via step 308, and the process returns back to step 302 to measure additional heart rates of the user. If no, then High_hr_flag is set to 0, via step 310. It is then determined whether the HRR is lower than another threshold (Threshold2) for more than the predefined percentage (P) of time (T1 seconds of the predetermined time period T2), via step 312.

If yes, (HRR<Threshold2 over P), then Low_hr_flag is set to 1 denoting that a low heart rate has been detected, via step 314, and the process returns back to step 302 to measure additional heart rates of the user. If no, then Low_hr_flag is set to 0, via step 316, and the process returns back to step 302 to measure additional heart rates of the user. In one embodiment, the Threshold1 is 120 bpm, the Threshold2 is 60 bpm, T2 seconds is 300 seconds, and P is 90%.

Figure 4:
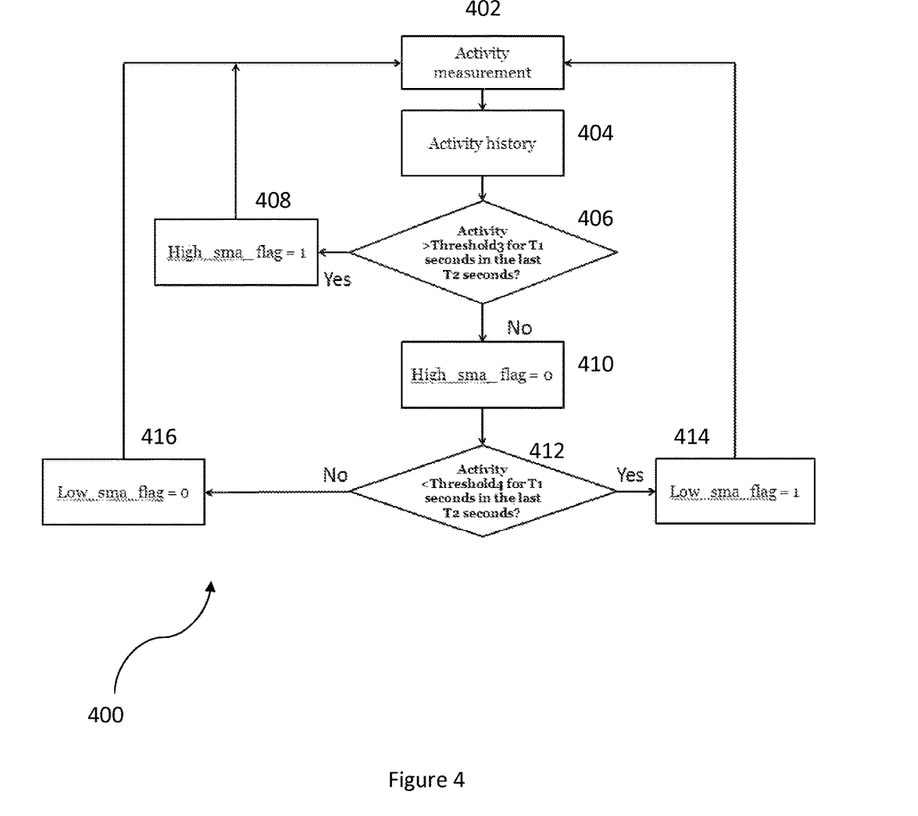
FIG. 4 illustrates a flowchart for measuring activity levels by a wireless sensor device in accordance with an embodiment.

In one embodiment, the wireless sensor device 100 calculates low and high activity levels using the embedded MEMS sensor. The activity levels can be calculated using a variety of methodologies including but not limited to: (1) a moving average of the sum of absolute values of bandpass-filtered x,y,z components of acceleration as measured by the MEMS accelerometer and (2) a moving average of the norm of the acceleration vector as measured by the MEMS accelerometer. In one embodiment, a one-second moving average is used with a bandpass filter having a denominator coefficient vector A=[1024, −992, 32], a numerator coefficient vector B=[496, 0, −496], and a sampling rate fs=62.5 Hz. In another embodiment, a one-second moving average is applied to the norm of the acceleration vector.

FIG. 4 illustrates a flowchart 400 for measuring activity levels by a wireless sensor device in accordance with an embodiment. In FIG. 4, the activity level (AL) of a user attached to the wireless sensor device is measured, via step 402, and the user's activity level history is analyzed and stored, via step 404. Activity level values over a predetermined time period (T2 seconds) are stored and used to determine low and high activity levels.

In FIG. 4, it is determined whether the AL is greater than a threshold (Threshold3) for more than a predefined percentage (P) of time (T1 seconds of the predetermined time period T2), via step 406. If yes (AL>Threshold3 over P), then High_sma_flag is set to 1 denoting that a high activity level has been detected, via step 408, and the process returns back to step 402 to measure additional activity levels of the user. If no, then High_sma_flag is set to 0, via step 410. It is then determined whether the AL is lower than another threshold (Threshold4) for more than the predefined percentage (P) of time (T1 seconds of the predetermined time period T2), via step 412.

If yes, (AL<Threshold4 over P), then Low_sma_flag is set to 1 denoting that a low activity level has been detected, via step 414, and the process returns back to step 402 to measure additional activity levels of the user. If no, then Low_sma_flag is set to 0, via step 416, and the process returns back to step 402 to measure additional heart rates of the user. In one embodiment, the Threshold3 is 2 gravitational acceleration (g; wherein g=9.81 m/s$^2$), the Threshold24 is 0.3 g, T2 seconds is 300 seconds, and P is 90%.

Figure 5:
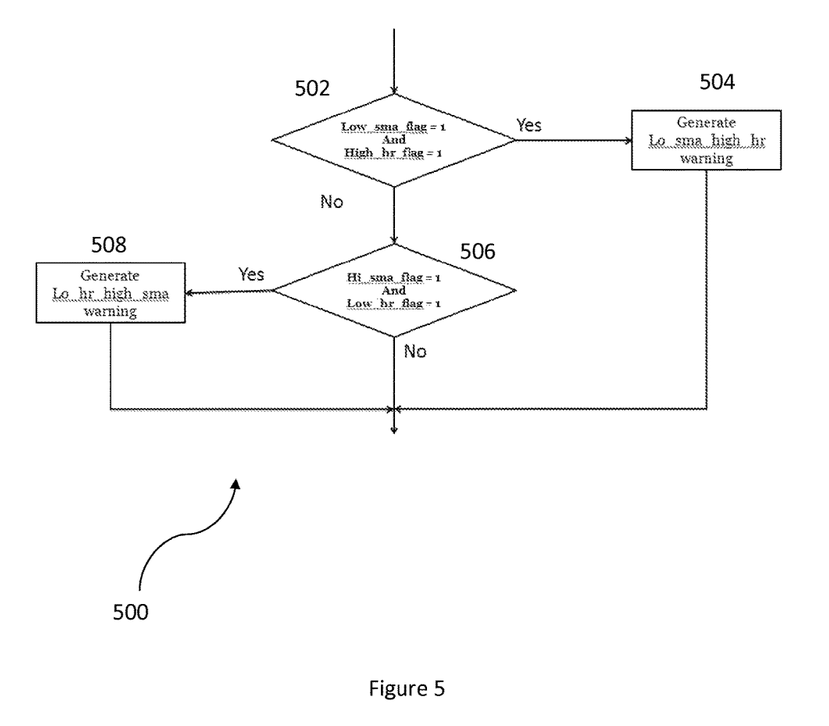
FIG. 5 illustrates a flowchart for generating warnings by a wireless sensor device in accordance with an embodiment.

In one embodiment, the computed heart rate and activity level of the user are utilized by the wireless sensor device to generate a warning. In one embodiment, a warning is generated if a low heart rate has been detected during a period that the user's activity level has been determined to be high. In another embodiment, a warning is generated if a high heart rate has been detected during a period that the user's activity level has been determined to be low. FIG. 5 illustrates a flowchart 500 for generating warnings by a wireless sensor device in accordance with an embodiment.

In FIG. 5, detected heart rate and activity level values and associated flags have been received by the wireless sensor device. It is then determined whether Low_sma_flag=1 and whether High_hr_flag=1, via step 502. If yes (both Low_sma_flag and High_hr_flag are set to 1 denoting the user has a high heart rate over a period of low activity which could be abnormal), a Low_sma_high_hr warning is generated, via step 504. If no, it is determined whether High_sma_flag=1 and whether Low_hr_flag=1, via step 506. If yes (both High_sma_flag and Low_hr_flag are set to 1 denoting the user has a low heart rate over a period of high activity which could be abnormal), a Low_hr_high_sma warning is generated, via step 508.

Figure 6:
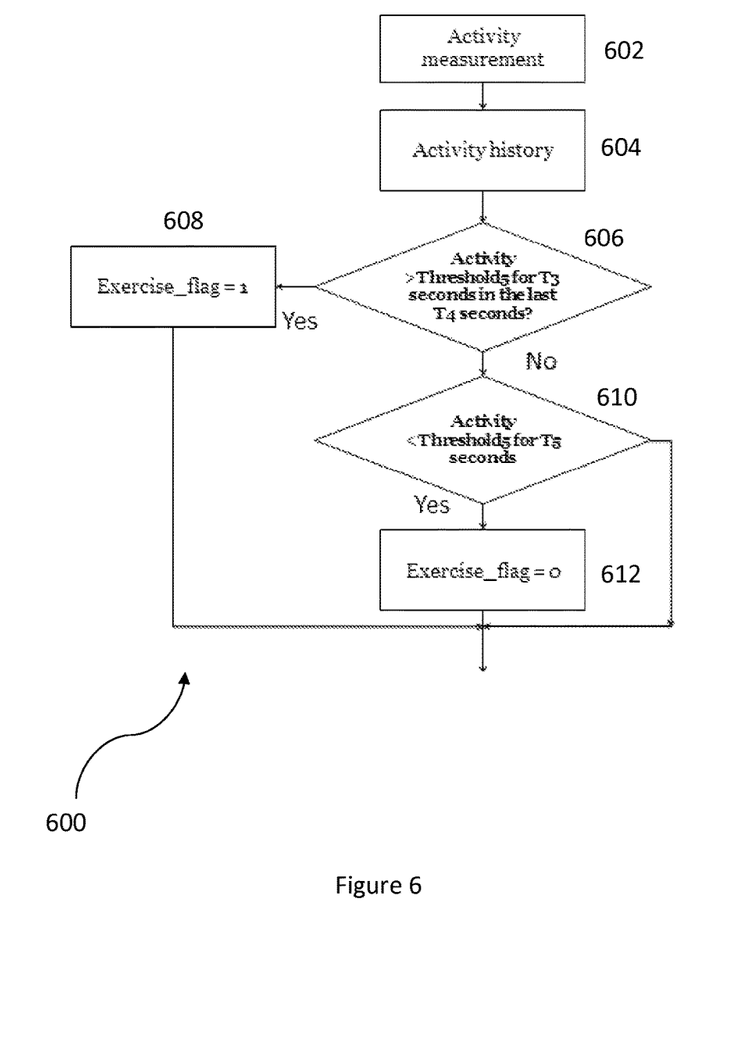
FIG. 6 illustrates a flowchart for measuring recovery heart rate in accordance with an embodiment.

In one embodiment, the computed heart rate and activity level of the user are utilized by the wireless sensor device to measure the recovery heart rate. The recovery heart rate is the heart rate measured at a fixed (or reference) period after ceasing activity. A greater reduction in heart rate after exercise during the reference period typically indicates a better conditioned heart. FIG. 6 illustrates a flowchart 600 for measuring recovery heart rate in accordance with an embodiment.

In FIG. 6, the activity level (AL) of a user attached to the wireless sensor device is measured, via step 602, and the user's activity level history is analyzed and stored, via step 604. To automatically measure and keep track of the user's recovery heart rate, the user's activity level history is stored over a predetermined time period (T4 seconds). The user's activity level history can also be stored over a plurality of varying predetermined time periods. It is determined whether the AL is greater than a threshold (Threshold4) for more than a predefined percentage (P) of time (T3 seconds of the predetermined time period T4), via step 606.

If yes (AL>Threshold4 over P), then Exercise_flag is set to 1 denoting that the user is exercising for a prolonged period of time, via step 608. In one embodiment, Threshold 4 is 4 g, T4 is 900 seconds, and P is 70%. If no (AL is not >Threshold4 over P), then it is determined whether the AL is less than a threshold (Threshold5) and stays below the Threshold5 for a predetermined time period (T5 seconds), via step 610. If yes, (AL<Threshold5 for T5 seconds), Exercise_flag is set to 0 denoting that the user is not exercising, via step 612. In one embodiment, Threshold5 is 0.6 g and T5 is 10 seconds.

In one embodiment, after calculating the heart rate of the user at various activity levels and detecting whether the user is exercising, the wireless sensor device analyzes calculated heart rate history during periods of detected exercise. A history of the heart rate values are stored during the periods of time when exercise is detected. Recovery heart rate is calculated based upon the heart rate difference between the time exercise stops (e.g. Exercise_flag is reset from 1 to 0) and a predetermined time period (T6 seconds). In one embodiment, T6 is 60 seconds.

Figure 7:
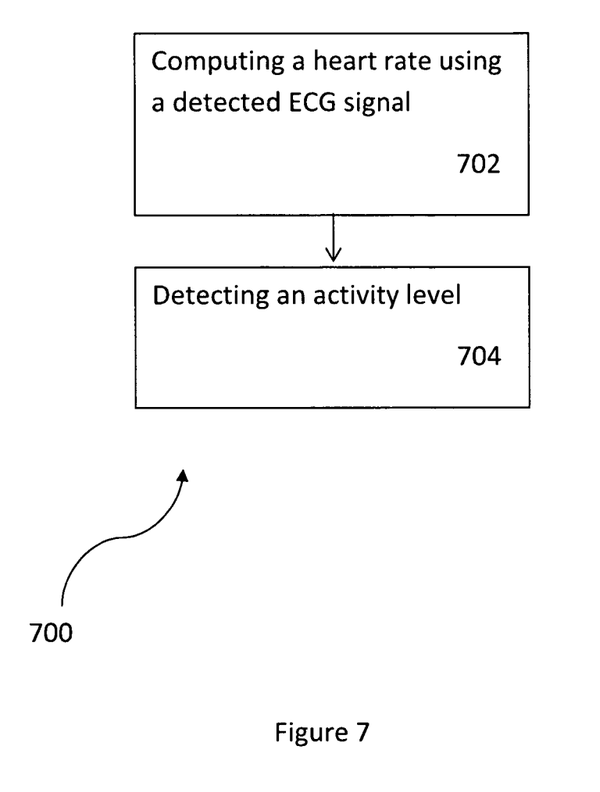
FIG. 7 illustrates a method for contextual heart rate monitoring in accordance with an embodiment.

FIG. 7 illustrates a method 700 for contextual heart rate monitoring in accordance with an embodiment. The method 700 comprises computing a heart rate using a detected ECG signal, via 702, and detecting an activity level, via 704. In one embodiment, a wireless sensor device attached to the chest of a user is utilized to detect the ECG signal and the activity level. In one embodiment, the heart rate is computed over a predetermined time period and the activity level is simultaneously detected over the same predetermined time period.

In one embodiment, the method 700 includes generating a warning based upon both the heart rate and the activity level. The warning is generated when the heart rate is above a first threshold denoting a fast beating heart and the activity level is below a second threshold denoting a non-active (e.g. presence of exercise not detected) user activity level. The warning is also generated when the heart rate is below a first threshold denoting a slow beating heart and the activity level is above a second threshold denoting an active (e.g. presence of exercise detected) user activity level.

In one embodiment, the method 700 includes automatically and continuously computing a recovery heart rate when the exercise ceases or is no longer detected by the wireless sensor device. The computation involves a heart rate difference between the time at which the exercise ceases and a later predetermined time period (e.g. 60 seconds after the exercise stops). In one embodiment, the method 700 includes tracking the recovery heart rate over a predetermined time period to determine various types of cardiovascular disease. In one embodiment, the method 700 includes determining a low and high threshold for the heart rate using the user's age information and present heart rate values that are set by the user.

As above described, the method and system allow for contextual heart rate monitoring and for automatically measuring a user's recovery heart rate. By detecting an ECG signal to compute both a user's past and current heart rate values and by detecting a user's past and current activity levels via an embedded MEMS sensor, a wireless sensor device monitors and stores heart rate values during periods of high activity (e.g. exercise). When exercise ceases, the wireless sensor device detects the lack of activity and automatically begins computation of the recovery heart rate.

A method and system for contextual heart rate monitoring has been disclosed. Embodiments described herein can take the form of an entirely hardware implementation, an entirely software implementation, or an implementation containing both hardware and software elements. Embodiments may be implemented in software, which includes, but is not limited to, application software, firmware, resident software, microcode, etc.

The steps described herein may be implemented using any suitable controller or processor, and software application, which may be stored on any suitable storage location or computer-readable medium. The software application provides instructions that enable the processor to cause the receiver to perform the functions described herein.

Furthermore, embodiments may take the form of a computer program product accessible from a computer-usable or computer-readable storage medium providing program code or program instructions for use by or in connection with a computer or any instruction execution system. For the purposes of this description, a computer-usable or computer-readable storage medium can be any apparatus that can contain, store, communicate, propagate, or transport the program for use by or in connection with the instruction execution system, apparatus, or device.

The computer-readable storage medium may be an electronic, magnetic, optical, electromagnetic, infrared, semiconductor system (or apparatus or device), or a propagation medium. Examples of a computer-readable storage medium include a semiconductor or solid state memory, magnetic tape, a removable computer diskette, a random access memory (RAM), a read-only memory (ROM), a rigid magnetic disk, and an optical disk. Current examples of optical disks include DVD, compact disk-read-only memory (CD-ROM), and compact disk-read/write (CD-RAN).

Although the present invention has been described in accordance with the embodiments shown, one of ordinary skill in the art will readily recognize that there could be variations to the embodiments and those variations would be within the spirit and scope of the present invention. Accordingly, many modifications may be made by one of ordinary skill in the art without departing from the spirit and scope of the appended claims.

What is claimed is:

1. A method for contextual heart rate monitoring, the method comprising:
   detecting an ECG signal using a wireless sensor device in a patch form factor comprising at least one electrode, wherein the wireless sensor device is coupled externally to a user;
   determining a heart rate using the ECG signal;
   detecting an activity level; and
   generating one or more warnings based upon the heart rate and the activity level, wherein the one or more warnings include
a first warning when the heart rate is above a first threshold and the activity level is below a third threshold, and
a second warning when the heart rate is below a second threshold and the activity level is above a fourth threshold,
wherein the first threshold, second threshold, third threshold and fourth threshold are defined by activity measured against heart rate reserve, wherein the heart rate reserve is defined as (Heart Rate (HR)−Resting Heart Rate)/(Maximum Heart Rate−Resting Heart Rate).

2. The method of claim 1, wherein the heart rate is calculated over a predetermined time period and the activity level is detected over the predetermined time period.

3. The method of claim 1, wherein the first threshold is a high heart rate threshold, the second threshold is a low heart rate threshold, the third threshold is a high activity level threshold, and the fourth threshold is a low activity level threshold.

4. The method of claim 1, wherein exercise is detected when the activity level is above the fourth threshold.

5. The method of claim 4, further comprising:
calculating a recovery heart rate when the exercise ceases.

6. The method of claim 5, wherein the calculating of the recovery heart rate further comprises:
calculating another heart rate a predetermined time period after the exercise ceases,
wherein the recovery heart rate is a difference between the heart rate when the exercise ceases and the another heart rate at a predetermined time period after the exercise ceases.

7. The method of claim 5, further comprising:
tracking the recovery heart rate over another predetermined time period to determine cardiovascular disease.

8. The method of claim 1, further comprising:
determining both the low heart rate threshold and the high heart rate threshold using age information and preset values.

9. A system for contextual heart rate monitoring, the system comprising:
a wireless sensor device in a patch form factor coupled externally to a user, wherein the wireless sensor device comprising at least one electrode, a sensor to detect an ECG signal of the user, a processor coupled to the sensor, and a memory device coupled to the processor, wherein the memory device stores an application which, when executed by the processor, causes the processor to:
determine a heart rate using the ECG signal;
detect an activity level; and
generate one or more warnings based upon the heart rate and the activity level,
wherein the one or more warnings include
a first warning when the heart rate is above a first threshold and the activity level is below a third threshold, and
a second warning when the heart rate is below a second threshold and the activity level is above a fourth threshold,
wherein the first threshold, second threshold, third threshold and fourth threshold are defined by activity measured against heart rate reserve, wherein the heart rate reserve is defined as (Heart Rate (HR)−Resting Heart Rate)/(Maximum Heart Rate−Resting Heart Rate).

10. The system of claim 9, wherein the heart rate is calculated over a predetermined time period and the activity level is detected over the predetermined time period.

11. The system of claim 9, wherein the first threshold is a high heart rate threshold, the second threshold is a low heart rate threshold, the third threshold is a high activity level threshold, and the fourth threshold is a low activity level threshold.

12. The system of claim 9, wherein exercise is detected when the activity level is above the fourth threshold.

13. The system of claim 12, wherein the application further causes the processor to:
calculate a recovery heart rate when the exercise ceases.

14. The system of claim 13, wherein to calculate the recovery heart rate further comprises to:
calculate another heart rate a predetermined time period after the exercise ceases,
wherein the recovery heart rate is a difference between the heart rate when the exercise ceases and the another heart rate at a predetermined time period after the exercise ceases.

15. The system of claim 13, wherein the application further causes the processor to:
track the recovery heart rate over another predetermined time period to determine cardiovascular disease.

16. The system of claim 9, wherein the application further causes the processor to:
determine both the low heart rate threshold and the high heart rate threshold using age information and preset values.

* * * * *